(12) United States Patent
Paden et al.

(10) Patent No.: US 11,826,503 B2
(45) Date of Patent: Nov. 28, 2023

(54) MEDICAL FLUID CASSETTES AND RELATED SYSTEMS

(71) Applicants: Georgia Tech Research Corporation, Atlanta, GA (US); Emory University, Atlanta, GA (US); Children's Healthcare of Atlanta, Inc., Atlanta, GA (US)

(72) Inventors: Matthew Paden, Atlanta, GA (US); Sivakkumar Arjunon, Atlanta, GA (US); Ajit Yoganathan, Atlanta, GA (US); Brian Walsh, Alpharetta, GA (US)

(73) Assignees: Children's Healthcare of Atlanta, Inc., Atlanta, GA (US); Emory University, Atlanta, GA (US)

(*) Notice: Subject to any disclaimer, the term of this patent is extended or adjusted under 35 U.S.C. 154(b) by 623 days.

(21) Appl. No.: 16/762,281

(22) PCT Filed: Nov. 13, 2018

(86) PCT No.: PCT/US2018/060726
§ 371 (c)(1),
(2) Date: May 7, 2020

(87) PCT Pub. No.: WO2019/094927
PCT Pub. Date: May 16, 2019

(65) Prior Publication Data
US 2020/0297910 A1    Sep. 24, 2020

Related U.S. Application Data

(60) Provisional application No. 62/585,310, filed on Nov. 13, 2017.

(51) Int. Cl.
*A61M 1/30* (2006.01)
*A61M 1/36* (2006.01)

(52) U.S. Cl.
CPC ............ *A61M 1/306* (2014.02); *A61M 1/302* (2014.02); *A61M 1/3606* (2014.02);
(Continued)

(58) Field of Classification Search
CPC ........ A61M 1/14; A61M 1/302; A61M 1/306; A61M 1/3606; A61M 2205/121;
(Continued)

(56) References Cited

U.S. PATENT DOCUMENTS

| | | |
|---|---|---|
| 2004/0019313 A1 | 1/2004 | Childers et al. |
| 2009/0107902 A1* | 4/2009 | Childers ............ A61M 1/1621 210/321.71 |

FOREIGN PATENT DOCUMENTS

| | | |
|---|---|---|
| WO | 2009/055639 A2 | 4/2009 |
| WO | 2016/039822 A1 | 3/2016 |
| WO | 2019/094927 A1 | 5/2019 |

\* cited by examiner

*Primary Examiner* — Dirk R Bass
(74) *Attorney, Agent, or Firm* — Smith, Gambrell & Russell LLP; Judy Jarecki-Black

(57) ABSTRACT

Systems relate to a reusable console system that can be used with a plurality of different types of disposable cassettes. The cassettes may be structured for different therapies, different fluid volumes, among others, or a combination thereof. The disposable cassette may include a plurality of fluid circuits. Each circuit may include a pump chamber disposed along the path. The disposable cassette and the panel of a console may be configured to mate so that each of the one or more actuators of the console align with a pump chamber of the disposable cassette. The console may be configured to control a flow of the fluid in the path in the cassette when the disposable cassette is mated on the panel. Because the console can be mated with different cassettes,
(Continued)

the system can efficiently and accurately deliver different medical fluid therapies and/or different patient populations (e.g., pediatric and adult).

18 Claims, 9 Drawing Sheets

(52) U.S. Cl.
CPC . *A61M 2205/121* (2013.01); *A61M 2205/125* (2013.01); *A61M 2205/3334* (2013.01); *A61M 2205/75* (2013.01)

(58) Field of Classification Search
CPC .... A61M 2205/125; A61M 2205/3334; A61M 2205/75
See application file for complete search history.

800

| POWER | SETUP | PRIME | TREAT | HISTORY | GRAPHS |

PATIENT WEIGHT — XX kg

TREATMENT MODE — CWH ▽

LINE TEMPERATURE — xx °C

OF DIALYSATE BAGS — xx

DIALYSATE BAG SIZE — xx L

AUTOMATED FLUSH BACK VOLUME — xx CC

☐ Provide Inputs
☐ Insert Cassette
☐ Confirm Mode
☐ Priming Fluid
☐ Prime

NEXT →

START | CHANGE FILTER | SILENCE ALARM | STOP

| POWER | SETUP | PRIME | TREAT | HISTORY | GRAPHS |

BLOOD FLOW — mL/min

ULTRAFILTRATE FLOW — mL/hr

DIALYSATE FLOW — mL/hr

FILTER LIFE: X HOURS REMAINING

NEXT →

START | CHANGE FILTER | SILENCE ALARM | STOP

| POWER | SETUP | PRIME | TREAT | HISTORY | GRAPHS |

TREATMENT PARAMETERS:

Arterial Upper Limit xx △ ▽        Effluent Upper Limit xx △ ▽
Arterial Lower Limit xx △ ▽        Effluent Lower Limit xx △ ▽
venous Upper Limit  xx △ ▽
venous Lower Limit  xx △ ▽

RETURN TO TREAT

FILTER LIFE: X HOURS REMAINING

START | CHANGE FILTER | SILENCE ALARM | STOP

| POWER | SETUP | PRIME | TREAT | HISTORY | GRAPHS |

Arterial Line Pressure            Line Temperature: xx °C △ ▽
                                  Blood Flow: xx mL/min △ ▽
venous Line Pressure              UltraFiltrate Flow: xx mL/hr △ ▽
                                  Dialysate Flow: xx mL/hr △ ▽
Effluent Line Pressure
                                  Transmembrane Pressure: xx mmHg
                                  Filtrate Fraction: xx%
Change Pressure Parameters 🔒
                                  DATE: 00/00/0000
                                  TIME: 00:00
FILTER LIFE: X HOURS REMAINING    MODE: XXXX

START | CHANGE FILTER | 🔒 | SILENCE ALARM | STOP

FIG. 11

MEDICAL FLUID CASSETTES AND RELATED SYSTEMS

CROSS REFERENCE TO RELATED APPLICATIONS

This application is a national stage application, filed under 35 U.S.C. § 371, of International Patent Application No. PCT/US2018/060726 filed on Nov. 13, 2018, which claims benefit of and priority to U.S. Provisional Patent Application No. 62/585,310 filed on Nov. 13, 2017, which are incorporated herein by reference in their entirety.

FIELD OF THE INVENTION

This invention is generally directed to systems and methods for medical fluid treatment therapies.

BACKGROUND OF THE INVENTION

Medical fluid treatment therapies are generally used to treat loss of renal function or renal failure. A person's renal system can fail due to disease, injury or other causes (e.g., as complications associated with extracorporeal membrane oxygenation (ECMO) treatment). During renal failure or loss of renal function, toxic end products of metabolism (e.g., urea, creatinine, uric acid, and others) can accumulate in blood and tissues because the balance of water, minerals and the excretion of daily metabolic load can be reduced or no longer possible.

Renal support can be provided by a continuous renal replacement therapy (CRRT), including but not limited to slow continuous ultrafiltration (SCUF), continuous venovenous hemodialysis (CVVHD), continuous venovenous hemofiltration (CVVH) or continuous venovenous hemodiafiltration (CVVHDF). These therapies are designed to remove metabolic waste and excess fluid from patient in fluid overload and those who need renal support. These therapies provide continuous fluid, electrolyte and toxin clearance even in the absence of adequate native renal function via convective or dialytic processes through a permeable membrane.

CRRT is a common renal replacement therapy for critically ill and hemodynamically unstable patients in the pediatric intensive care unit. However, current systems are not specifically designed for both adult and pediatric use. Generally, devices approved for adults are used to treat children, who require smaller volumes. Additionally, current systems require multiple tube connections and thus set-up can be time-consuming and can be error-prone.

Thus, there is a need for systems and disposable components configured for efficient, accurate and flexible use.

SUMMARY

This disclosure generally relates to systems, disposable cassettes, and disposable kits configured for medical fluid treatment therapies. The systems may relate to a reusable console system that can be used with a plurality of different types of disposable cassettes. The cassettes may be structured for different therapies, different fluid volumes, among others, or a combination thereof. Because the console can be mated with different cassettes, the system can efficiently and accurately deliver different medical fluid therapies to different patient populations (e.g., pediatric and adult).

In some embodiments, tire systems may include a console and at least one disposable cassette. The console may have a panel. The console may include one or more actuators disposed between a first pinch valve and a second pinch valve. The one or more actuators may be configured to move with respect to the panel. The disposable cassette may be configured to mate with the panel. The disposable cassette may include a plurality of fluid circuits. Each fluid circuit may include a path being defined by one and more inlets and outlets in which a fluid flows, and a pump chamber disposed between a first valve receiving member and a second valve receiving member along the path.

In some embodiments, the disposable cassette and the panel may be configured to mate so that each of the one or more actuators align with a pump chamber and the corresponding first pinch valve and the second pinch valve align and interface with the corresponding first valve receiving member and the second valve receiving member. The console may be configured to control the movement of the actuator and the first and the second pinch vales to control a flow of the fluid in the path when the disposable cassette and the panel are mated.

In some embodiments, the disposable cassette may include one or more pressure sensors disposed along the path of one or more fluid circuits and an electrical communication interface that communicates with each pressure sensor. The console may include one or more fluid sensors to measure fluid characteristics of the flow alone the path of one or more fluid circuits and an electrical communication interface that is complimentary to the electrical communication interface of the disposable cassette. In some embodiments, when the disposable cassette and the panel are mated, the electrical communication interface of the disposable cassette may be configured to transmit the pressure to the console via the electrical communication interface of the console.

In some embodiments, the system may further include a filter and one or more containers. The cassette may be configured to be disposed on the panel between the filter and the one or more containers so that the filter and the one or more containers are disposed adjacent to a first side and a second side of the cassette, respectively In some embodiments, the system may further include a dialysate circuit configured to connect to the filter.

In some embodiments, each fluid circuit may be configured for unidirectional fluid flow along the path. In some embodiments, the fluid circuits may include a blood circuit, an ultrafiltrate circuit, a replacement fluid circuit and a return circuit. In some embodiments, the blood circuit may include an inlet and an outlet disposed on the first side. In some embodiments, a length of the path, of the blood circuit may be shorter than a length of the paths of the ultra filtrate circuit, the replacement fluid circuit and the return circuit. In some embodiments, the fluid circuits may be disposed with respect to the top of the cassette when mated with the console as follows: she blood circuit, the ultrafiltrate circuit, the replacement fluid circuit and the return circuit.

In some embodiments, the methods may include a method of delivering a medical fluid delivery therapy. In some embodiments, the method may include providing a disposable cassette and a console. In some embodiments, the method may include mating a disposable cassette with a panel of a console. The disposable cassette may include a console having a panel. The disposable cassette may include a plurality of fluid circuits. Each fluid circuit may include a path being defined by one or more inlets and outlets in which a fluid flows, and a pump chamber disposed between a first valve receiving member and a second valve receiving member along the path. The pump chamber may include a flexible membrane and a rigid portion.

In some embodiments, the console may include one or more actuators disposed between a first pinch valve and a second pinch valve. The one or more actuators may be configured to move between a resting position and an upstroke position with respect to the panel. In some embodiments, when the disposable cassette is mated with the panel, the actuator may align with the flexible membrane pump chamber, and the corresponding first pinch valve and the second pinch valve may align and interface with the respective first valve receiving member and the second valve receiving member.

In some embodiments, the method may include causing the first pinch valve to open and the second pinch valve to close to draw a fluid into one of the fluid circuits. In some embodiments, the method may further include causing the first pinch valve to close and the second pinch valve to open and the corresponding actuator to contact the flexible membrane and to extend toward the rigid portion.

In some embodiments, the disposable cassettes may include a disposable cassette configured to be mated with a console. In some embodiments, the disposable cassette may include a housing. In some embodiments, the cassette may also include a plurality of fluid circuits disposed within the housing. Each of the plurality of fluid circuits may include a path being defined by one or more inlets and outlets disposed in the housing. Each fluid circuit may be configured for unidirectional fluid flow along the path and the fluid circuits may include a blood circuit, an ultrafiltrate circuit, a replacement fluid circuit and a return circuit. Each fluid circuit may include a pump chamber disposed between a first valve receiving member and a second valve receiving member. In some embodiments, one or more of the fluid circuits may include a pressure sensor configured to detect pressure within the one or more of the fluid circuits. In some embodiments, the cassette may include an electrical communication interface configured to transmit the pressure from the pressure sensor to a console system.

In some embodiments, the cassette may include a first side and an opposing second side. The blood circuit may include an inlet and an outlet disposed on the first side. In some embodiments, a length of the path of the blood circuit may be shorter than a length of the paths of the ultrafiltrate circuit, the replacement fluid circuit and the return circuit. In some embodiments, the fluid circuits may be disposed with respect to the top of the housing as follows: the blood circuit, the ultrafiltrate circuit, the replacement fluid circuit and the return circuit.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

FIGS. 8-12 show examples of system-generated user interfaces according to embodiments.

DETAILED DESCRIPTION OF THE EMBODIMENTS

Figure 1:
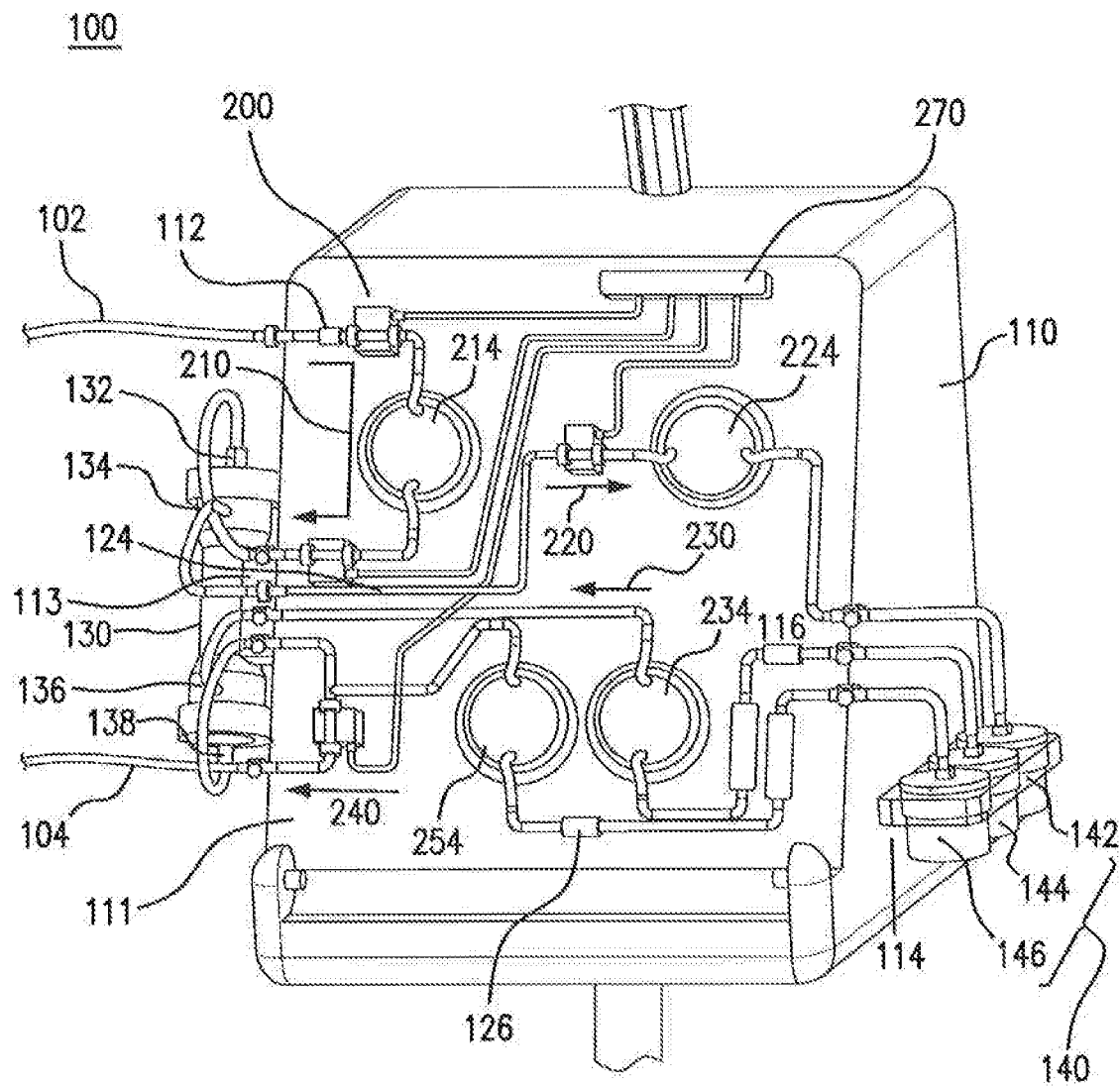
FIG. 1 shows a fluid delivery system according to embodiments.

In the following description, numerous specific details are set forth such as examples of specific components, devices, methods, etc., in order to provide an understanding of embodiments of the disclosure. It wilt be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosure relates to systems, disposable cassettes, and kits for medical fluid treatment therapies, such as extracorporeal treatment therapies, to assist patients with severe organ dysfunction. According to embodiments, the system can be configured for different medical fluid treatment therapies or extracorpeal treatment systems, different volumes, among others, or any combination thereof. In some embodiments, the medical fluid treatment systems, disposable cassettes, and kits may be capable of providing any CRRT therapy, such as slow continuous ultrafiltration (SCUF) therapy, continuous veno-venous hemofiltration (CVVH) therapy, continuous veno-venous hemodiafiltration (CVVHDF) therapy, continuous veno-venous hemodialysis (CVVHD) therapy, among others, or any combination thereof. However, it will be understood that the systems, disposable cassettes, and kits can be structured for other types of medical fluid therapies, such as peritoneal dialysis, hemodialysis, hemofiltration, hemodiafiltration, therapeutic plasma exchange, cytopheresis, hemoperfusion, other CRRT therapies, other dialysis treatment therapies, among others, or any combination thereof.

In some embodiments, the system may include a reusable console system that can be used with a plurality of different types of disposable cassettes. In some embodiments, the cassettes may be structured for different therapies, different fluid volumes, among others, or a combination thereof. A specific therapy can be chosen by simply selecting that corresponding cassette and thus set-up can be simplified. In this way, the system can be set up efficiently for the therapy and can deliver the therapy accurately between different patient populations including those of child and adult. Additionally, because the cassettes are disposable and can be discarded after single use, risks associated with contamination can be reduced.

FIGS. 1-6 show a fluid therapy system 100 according to embodiments. As shown in FIG. 1, the system 100 may include a console 110 and a disposable delivery set. In some embodiments, the delivery set may include but is not limited to an arterial blood line 102, a venous blood line 104, a filter 130, one or more disposable cassettes 200, one or more containers, conduits (e.g., tubing) to connect the port(s) of the cassette 200 to the ports of the filter and/or containers, among others, or my combination thereof.

In some embodiments, the delivery set may be single use, disposables. In some embodiments, one or more of the components may be reusable. In some embodiments, the delivery set may be packaged as a kit.

The console 110 may be configured to accept and operate with one or more disposable cassettes to deliver a medical fluid treatment therapy. In some embodiments, the mode of operation of the console 110 may depend on the cassette mated with the console 110. In some embodiments, the one or more cassettes may include cassettes configured for one or more different treatment therapies, one or more cassettes configured for different patient populations, one or more cassettes configured for console diagnostics (also referred to as "service cassette"), among others, or any combination thereof. By way of example, the cassettes for different treatment therapies may include cassettes configured for all CRRT therapies (e.g., SCUP, CVVH, CVVHD, and CVVHDF), cassettes configured for some therapies, cassettes configured for specific CRRT therapies (e.g., SCUF and CVVH), among others, or any combination thereof. Each of these different therapy cassettes may also be configured for different patient populations. For example, the cassettes configured for CRRT therapies and the cassettes configured far specific CRRT therapies may also include cassettes sized for use with an adult patient and cassettes sized for use with a pediatric patient. In this example, the one or more cassettes may include four different therapy cassettes (e.g., two different cassettes for adult patient population and two different cassettes for pediatric patient population). The 5 one or more cassettes are not limited to four different therapy cassettes and may include more or less different cassettes.

In some embodiments, the cassette 200 (e.g., cassette housing) may be color-coded and/or other indicia according to therapy type (e.g., treatment mode and/or patient population). According to some embodiments, a portion or combination of the disposable set may be sold as a kit. By way of example, the kit may include the cassette 200, the filter 130, the one or more containers 140, conduits (e.g., tubing) for connection of the ports of the cassette to the filter 130, the service cassette, priming fluid, among others, or any combination thereof.

The console 110 can be configured to control the medical fluid treatment therapy by controlling and monitoring operation of the fluid through the flow paths included in a cassette. In some embodiments, the console 110 and/or the disposable cassette 200 may include one or more sensors and/or detectors. The sensors and/or detectors may include but are not limited to fluid sensors/detectors, operation sensors/detectors, among others, or a combination thereof. It will be understood that the console 110 and/or the cassette 200 are not limited to the sensors and/or detectors as shown and as described. The console 110 and/or cassette 200 may include different configuration of the sensors, additional sensors, alternative sensors, and/or any combination thereof. For example, the console 110 and/or the cassette 200 may include a flow meter, a volume sensor, among others, or a combination thereof.

FIG. 1 shows an example of the cassette 200 configured for all CRRT therapies mated with the console 110 and may system configured for CVVHD or CVVHDF modes. However, it is understood that the console 110, the cassette 200 and the other components of the disposable set may be modified for different therapies and/or patient populations. Some non-limiting examples of these modifications are discussed herein.

In some embodiments, the console 110 may include a panel or surface 111 of the console (also referred to as "mating panel") on which the cassette 200 may be mated. In some embodiments, the console 110 may be modular and/or portable. As shown in FIG. 1, the console 110 may be disposed, for example, with respect to a cart and/or table, such that cassette 200 can mate vertically with the panel 111 of the console 110. In some embodiments, the console 110 may be disposed, for example, with respect to a cart and/or table, in a different position. For example, the console 200 may also be disposal such that the cassette can mate horizontally with the mating panel 111 of the console 110.

In some embodiments, the console 110 and/or the cassette 200 may be configured to mechanically or magnetically mate. By way of example, the console 110 and/or the cassette 200 may include one or more mechanical and/or magnetic members configured to removably fix the cassette 200 to the panel 111 at a specific position (not shown). By way of example, the mechanical member(s) may include a hinged mechanism, a latch mechanism, a slide-lock, a snap on mechanism, among others, or a combination thereof. In some embodiments, the magnetic members may include complimentary magnets disposed on the console 110 and the cassette 200 at corresponding locations.

In some embodiments, the console 110 may additionally and/or alternatively include a hinged door that secures the cassette 200 to the panel 111. For example, the door of the console may include a latching mechanism, such as a clamp, that interacts with the cassette 200 to fix the cassette 200 with respect to the console 110.

In some embodiments, the console 110 and/or the cassette 200 may be configured to actively and/or passively remove the mated or locked cassette 200. For example, the console 110 may be configured to be passive and the cassette may be configured to be removed manually, the console 110 may be configured to detach the cassette from the mated or locked-position, among others.

In some embodiments, when the cassette 200 is properly mated with the panel 111, the console 110 can mechanically and/or electrically interface with the cassette to control the medical fluid treatment by controlling and monitoring operation of the fluid through the flow paths included in the cassette. By way of example, when properly mated, the console 110 may include components that are configured to directly engage respective components of the cassette 200 by contact and/or indirectly engage respective components of the cassette 200 by being in a specific proximity. Additionally, the console 110 and the cassette 200 may include complimentary electrical communication interfaces configured so that the components (e.g., sensors) of the cassette 200 can communicate with the console 110. By way of example, the cassette 200 cart send any sensor signals to the console 110 via the electrical communication interfaces.

In some embodiments, the console 110 may include one or more receiving members in which the filter 130 and the one or more containers 140 can be disposed. The one or more receiving members may be any member configured to removably attach the filter 130 and the one or more containers 140 to the console 110. For example, as shown in the FIG. 1, the console 110 may include a first member 113 for the filter disposed on one side of the console and a second member 114 for the one or more containers 140 disposed on the opposing side of the console 110. In this example, the console 110 may be configured so that the cassette 200 is disposed between the filter 130 and the one or more containers 140 so that the fluid circuits of the cassette 200 are unidirectional. It will also be understood that the console 110 may have a different configuration of the receiving members, the filter, and/or the containers). For example, the receiving members may be disposed at different locations on the console 110.

In some embodiments, the filter 130 may be a semipermeable membrane that provides a system by which toxins from the blood can be removed via a method of convective drag or dialytic clearance. In some embodiments, the filter 130 may be a hemofilter, dialyzer, among others, or a combination thereof. The filter 130 may include a plurality of ports. In some embodiments, the ports may be Luer Lock connectors. In some embodiments, for example, if the filter is a hemofilter as shown in the FIG. 1, the filter may include a blood input port 132, an ultrafiltrate output port 134, a dialysate input port 136, a blood output port 138, among others, or any combination thereof.

In some embodiments, the one or more containers 140 may be any container, such as a reservoir or a bag that is needed to provide and/or collect a fluid. The one or more containers 140 disposed on the console 110 may depend on the medical fluid therapy. The one or more containers may include but are not limited to a container for ultrafiltrate collection 142, a container for dialysate fluid 144, and a container for replacement fluid 146, among others, or any combination thereof. In some embodiments, the arrangement of the one or more containers may be relative to the locations of the corresponding fluid circuits disposed in the cassette. In some embodiments, the containers 144 and 146 may be pro-filled with any dialysate solution and/or replacement fluid, respectively. The one or more containers may include different or additional containers). For example, the dialysate fluid container 144 may be omitted (for the CVVH mode). By way another example, the one or more containers 140 may additionally or alternatively include a container for a therapeutic (e.g., heparin).

Figure 2:
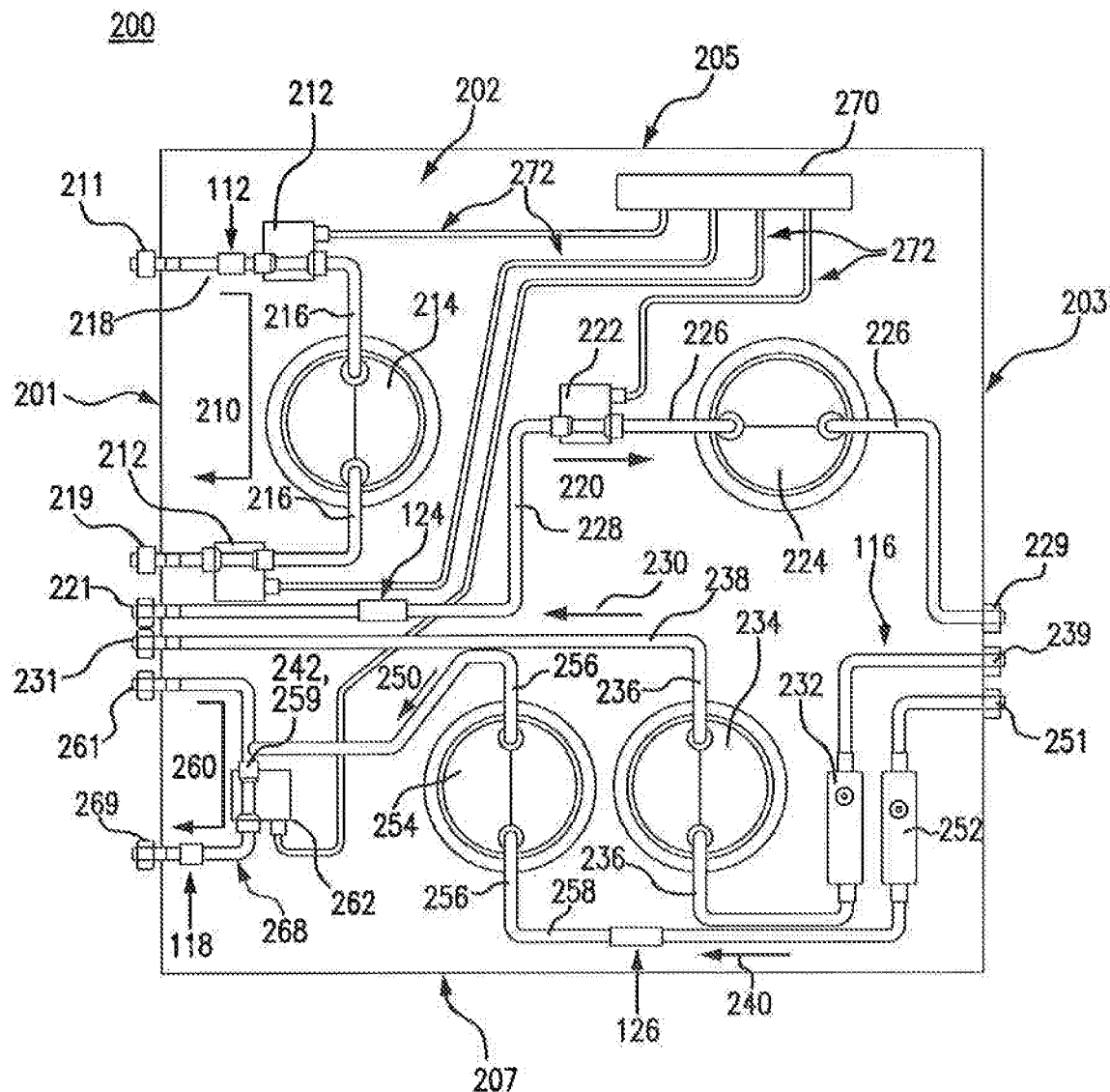
FIG. 2 shows the cassette shown in FIG. 1.

In some embodiments, the cassette 200 may be include a housing 202 in which the components are disposed, as shown in FIG. 2. In some embodiments, the housing 202 may have a rectangular shape. In other embodiments, the housing 202 may have a different shape. The housing 202 may at least partially cover the components of the cassette. The housing 202 may include one or more interface sections so that the components of the cassette (e.g., portions of the tubes, pump chambers, communication interface, etc.) can interface with the respective components (e.g., sensors, pumps, pinch valves, etc.) of the console 110. The interface sections may include anti may not be limited to include openings, notches, recesses, among others, or any combination thereof in the housing in which a specific portion of the cassette is exposed and is configured to be engaged by a corresponding component of the console 110. In some embodiments, the housing 202 may be a clam shell or a tray. In some embodiments, the housing 202 may be molded or otherwise formed from a suitable plastic or other material, such as a polymethyl methacrylate (PMMA) acrylic, or a cyclic olefin copolymer/ultra low density polyethylene (COC/ULDPE), and may be relatively rigid.

In some embodiments, the cassette 200 may include a plurality of fluid circuits. As used herein, the term "fluid circuit" of a cassette refers to a fluid path that is defined by an inlet, an outlet and one or more tubes and that is arranged in the cassette in which a fluid (e.g., replacement fluid, ultrafiltrate, blood, dialysate fluid, etc.) flows. In some embodiments, the fluid circuits may be arranged within the cassette for one or more unidirectional flow paths between the patient, filter, and/or containers. In some embodiments, the fluid circuits) may also include any combination of components, such as sensor(s), pump chamber(s), detectors/ traps, among others, disposed along its respective fluid path. The fluid circuits may include but are not limned to any combination of the following; an arterial blood circuit, an ultrafiltrate circuit, a dialysate circuit (CVVHD or CVVHDF modes), a fluid return circuit. In some embodiments, the arterial blood circuit may be a fluid path in which blood is circulated out of a patient (e.g., via an arterial line) and filtered by the filter. The ultra filtrate circuit may be the path where the waste products removed from the blood via the filler are collected by a container. The dialysate circuit may be the path where dialysate is added to the filter from a container for extraction of the waste products from blood. The return fluid circuit may include a first path where a volume of replacement fluid is added from the replacement fluid container to the filtered blood that converges with a second path, that returns the filtered blood from the filter and or the replacement fluid from the first path to the patient (e.g., via a venous line). The number and/or arrangement of the circuits may depend on the specific mode of the cassette. The number of fluid circuits included in the cassette may be modified according to the intended therapy corresponding to the cassette. By way of example, for the SCUF and/or CVVH modes, the cassette 200 may omit the dialysate circuit.

In some embodiments, the cassette 200 may include a plurality of input/output ports disposed on the sides of the housing 202. The ports may include but are not limited to ports configured to be connected to the arterial line, venous line, filter (via conduits), and one or more containers (via conduits). In some embodiments, the ports may be Luer Lock connectors. In some embodiments, the ports may be disposed on sides of the housing 202 closest to the respective inlet/outlet (e.g., line 102, filter 130, containers 140, and line 104). In some embodiments, the inlets and outlet ports of the cassette 200 may be disposed at or near the first side 201, which is the side closest to the tines 102 and 104 and the filter 130, and the opposing second side 203, which is the side closest to the containers 140. In some embodiments, the ports may also be disposed at or near the other sides 205 and 207. In some embodiments, the ports may define the beginning and end of the fluid path for each fluid circuit.

In some embodiments, the cassette 200 may include a blood circuit (also referred to as "blood circuit") 210. The blood circuit 210 may have a path that extends between an inlet port 211, disposed at the side 201, to receive blood from the patient (e.g., via arterial line 102) an outlet port 219, disposed at the side 201, that can connect to the port 132 of the filter 130 (via a conduit). In some embodiments, between the inlet 211 and the outlet 219, the blood circuit 210 may also include one or more pressure sensors 212 disposed on one or both sides of the pump chamber 214 to monitor the flow of the blood from the patient and along the path, a pump chamber 214 configured to mate with corresponding pump of the console 130, and one or more valve receiving members 216 disposed on opposite sides of the pump chamber 214 to mate with corresponding components (e.g., pinch valves of the console 110), and one or more conduits 218 (e.g., tubing) disposed through and/or in between the components of the circuit 210.

In some embodiments, the location and arrangement of the blood circuit 210 with respect to the cassette may be designed to minimize extra corporeal blood volume and thereby increase dialysis efficiency and performance, for example, in pediatric or smaller patients. By way of example, the length, surface area, among others, of the fluid path of the blood circuit 210 may be minimized, for example, by the reducing length of path, the blood circuit location on the cassette 200 with respect to the filter, patient, and/or inlet port, among others, or any combination thereof. As shown in FIG. 1, the inlet 211 and outlet 219 can be disposed on one side of the cassette 200 closest to the filter 130 so as to reduce the length of the path. In this, example, the length of the blood circuit path may therefore be the shortest path as compared to the other paths (e.g., ultrafiltrate, return, and/or dialysate).

In some embodiments, the cassette 200 may include an ultrafiltrate circuit 220. In some embodiments, the ultrafiltrate circuit 220 may have a path that extends between an inlet port 221, disposed at the side 201, that cart connect an outlet port 134 of the filter 130 (via a conduit) to receive the ultrafiltrate that was removed from the blood and an outlet port 229, disposed at the side 203, that can connect to the ultrafiltrate collection container 142 (via a conduit) to collect the filtered ultrafiltrate. As shown in FIGS. 1 and 2, the ultrafiltrate fluid circuit 220 may extend along the length of the cassette 200 between the filter 130 and the container(s) 140. In some embodiments, between the inlet 221 and the outlet 229, the circuit 220 may also include one or more pressure sensors 222 to monitor the pressure of the ultrafiltrate flowing within the circuit 220, a pump chamber 224 configured to mate with corresponding pump of the console 110, and one or more valve receiving members 226 disposed on opposite sides of the pump chamber 224 to mate with corresponding components (e.g., pinch valves) of the console 110, and one or more conduits 228 (e.g., tubing) disposed through and/or in between the components of the circuit. In some embodiments, the circuit 220 may include a pressure sensor 222 disposed on one or both sides of the pump chamber 224 to monitor the flow of the ultrafiltrate along the path.

In some embodiments, the cassette 200 may optionally include a dialysate circuit 230 (e.g., cassettes capable of CVVHD and/or CVVHDF therapies). The circuit 230 may have a path that extends between an inlet port 239, disposed at the side 203, that can connect to the dialysate fluid container 144 (via a conduit) and an outlet port 231, disposed at the side 201, that can connect to the inlet port 136 of the filter (via conduit) 130 to deliver a dialysate solution to the filter 130. The dialysate solution can be used to remove the toxins from the blood disposed in the filter, for example, in the CVVHD and/or CVVHDF modes. As shown in FIGS. 1 and 2, live dialysate circuit 230 may extend along the length of the cassette 200 between the filter 130 and the containers) 140. In some embodiments, between the inlet 239 and the outlet 231, the circuit 230 may also Include a pump chamber 234 configured to mate with corresponding pump of the console 110, and one or more valve receiving members 236 disposed on opposite sides of the pump chamber 234 to mate with corresponding components (e.g., pinch valves of the console 110), and one or more conduits 238 (e.g., tubing) disposed through and/or in between these components. In some embodiments, the dialysate circuit 230 may also include a bubble detector/trap 232 disposed between the inlet 239 and the pump 234. The bubble filter/trap 232 may be configured to prevent bubbles originating in the dialysate fluid container 144 from reaching the pump 234.

In some embodiments, the cassette 200 may include a return fluid circuit 240. In some embodiments, the circuit 240 may include two converging paths 250 and 260 to deliver the filtered blood and/or replacement fluid to the patient (via the venous line 104). In some embodiments, the first path may be between an inlet port 251, disposed at the side 203, that can connect to the replacement fluid container 146 (via a conduit) and an outlet 259 disposed along the second path 260 at converging point 242 so that the replacement fluid may be returned with and/or will tout the filtered blood via the second path 260. In some embodiments, between the inlet 251 and the outlet 259, the path 250 may also include a pump chamber 254 configured to mate with corresponding pump of the console 110, and one or more valve receiving members 256 disposed on opposite sides of the pump chamber 254 to mate with corresponding components (e.g., pinch valves of the console 110), and one or more conduits 258 (e.g., tubing) disposed through and/or in between these components. In some embodiments, the first path 250 may also include a bubble detector/filter/trap 252 disposed between the inlet 251 and the pump 254. The bubble detector/filter/trap 252 may be configured to prevent bubbles and/or particles originating in the replacement fluid container 146 from reaching the pump 254.

In some embodiments, the second path 260 may extend between an inlet port 261, disposed at the side 201, that can connect to the outlet port 138 of the filter 130 (via a conduit) to receive the filtered blood and an outlet port 269, disposed at the side 201, that delivers the filtered blood/replacement fluid to the patient (via venous line 104). In some embodiments, the path 260 may include a pressure sensor 262 disposed between the replacement fluid connection 259 and the outlet port 269 to monitor the flow of the replacement fluid and/or the filtered blood along the circuit.

In some embodiments, the one or inure pressure sensors (e.g., 212, 222, and 262) may be configured to monitor the flow of the fluid through the respective path. For example, the pressure sensor(s) can detect whether there are disruptions, such as clogs, within the path in which the sensor(s) are disposed. In some embodiments, the one or more pressure sensor(s) may be the same and/or different sensors. In some embodiments, the sensors may be a strain-gauge based pressure sensor. In some embodiments, each of the pressure sensors may include a transmission member 272 configured to transmit the signals from the respective pressure sensor to an electrical communication interface 270 of the cassette 200. By way of example, as shown in FIG. 1, the transmission member 272 may be configured for wired transmission (e.g., any wires and/or cables). In this example, each transmission member 272 may extend from the respective pressure sensor to the communication interface 270 of the cassette. In some embodiments, the transmission member may be a wireless transmitter. The pressure signals from the all of the pressure sensors can thereby be gathered at a single location, the communication interface 270 of the cassette, for output to the console 110.

In some embodiments, the pump chamber (e.g., 214, 224, 234, and 254) may include a flexible membrane configured to mechanically interface with respective pump disposed on the console 111. In some embodiments, the housing 202 may include an interface section (e.g., cut-out, opening, etc.) for the flexible membrane of each pump chamber.

Figure 3:
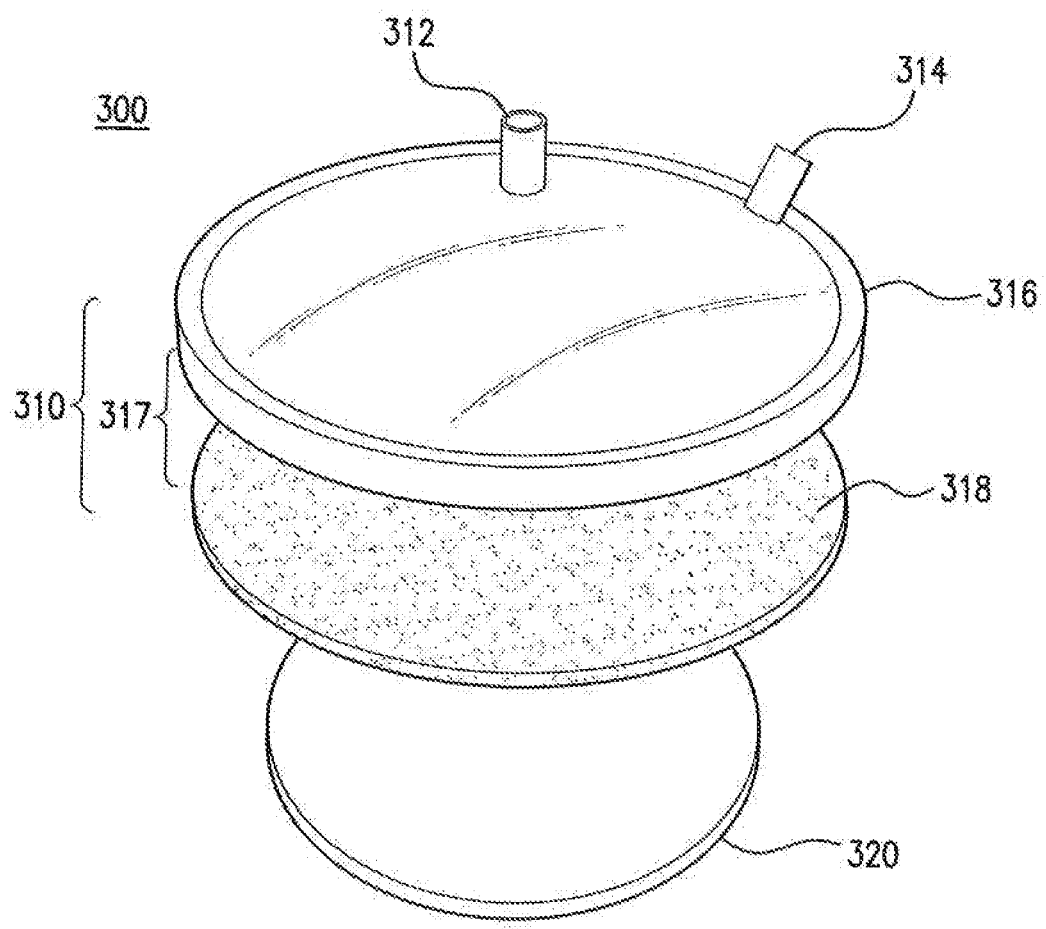
FIG. 3 shows an example of a partial portion of the pump interface between the cassette and console according to embodiments.

FIG. 3 shows an example of a pump chamber (e.g., 214, 224, 234, and 254) according to some embodiments. FIG. 3 shows an enlarged view 300 of the pump chamber 310 with respect to a pump 320 of the console 110 shown in FIGS. 1 and 2. As shown in live figure, the pump chamber 310 may include an inlet 312 and an outlet 314 that connects to the conduit(s) along the respective fluid circuit. In some embodiments, the pump chamber 310 may include a cap 316. In some embodiments, an inlet and an outlet may be disposed on the cap 316. In some embodiments, the cap 316 may be at least semi-rigid. In other embodiments, the cap 316 be may be made of other materials and rigidness. In some embodiments, the pump chamber 310 may include a bottom flexible membrane 318. The cap 316 and the flexible membrane 318 may be attached along the circumference so as to define an area 317 in which fluid may be held and passed along the fluid path via the conduits. The cassette housing 200 may include an interface section (e.g., cut-out, opening, etc.) for the bottom flexible membrane 318 and the bottom flexible membrane 318 may be configured to face the pump 320 disposed in the console panel 111.

In some embodiments, the pump chambers (e.g., 214, 224, 234, and 254) and/or conduits (tubing) disposed in the circuits may lie of the same size. It will be understood that the size of the pump chamber and conduits may depend on the patient population of the cassette. For example, for cassettes configured for pediatric patients, the pump chambers, the tubing, among others, may be smaller than the respective components disposed in cassettes configured for adult patients.

In some embodiments, the one or more valve receiving members (e.g., 216, 226, 236, and 256) may be an interface section (e.g., cut-out, opening, etc.) corresponding to a portion of the tubing on each side of the respective pump chamber. The one or more valve receiving members can be configured to be directly engaged by the console 110 via pinch valves disposed on tire console 110 to control the flow of the fluid through the respective pump chamber. In other embodiments, the cassette 200 may replace the one or more valve receiving members of each circuit with a different mechanism to control the flow through the respective pomp chamber. The different mechanism may include other valves including but not limited to other mechanically activated valves, electrically activated valves, among others, or any combination thereof. For example, the cassette 200 may include a valve disposed in the tubing on either side of each pump chamber. In this example, the cassette 200 may include (i) an inlet valve that can be configured to open when the pressure starts to drop and close when the pressure starts to increase and (ii) an outlet valve that can be configured to close when the pressure starts to drop and open when the pressure starts to increase. In another example, the cassette 200 may include mechanically activated pinch valve(s) that are attached to the cam shaft of the motor dun drives the pump.

In some embodiments, the fluid circuits may be disposed in the cassette 200 relative to the respective input/out let ports of the filter 130. As shown in FIG. 1, the circuits may be disposed in the following order from top to bottom: the blood circuit 210, the ultrafiltrate circuit 220, the dialysate circuit 230 (if included), and the return circuit 240. In this way, the paths can be more compact and thereby the system can more effectively and efficiently deliver the medical treatment therapies.

In some embodiments, the cassette 200 may include identification information. In some embodiments, the identification information may include but is not limited to identification number of the cassette, size of cassette (e.g., patient or pediatric), type of cassette (e.g., CVVH, CVVHD, CVVHDF, SCUF modes), among others, or any combination thereof in some embodiments, the identification information may be stored on a RFID tag or label disposed on the cassette 200. In some embodiments, the console 110 may include an identification device (RFID reader) capable of receiving and/or reading the identification information from the cassette 200.

In some embodiments, the electrical communication interface 270 configured to communicate with a complimentary electrical communication interface of the console 110 may be disposed above the fluid circuits. In other embodiments, the electrical communication interface 270 may be disposed at a different location.

In some embodiments, the cassette 200 may include different, more or less fluid circuits than those shown and described with respect to FIGS. 1 and 2 and the disposable set can be modified accordingly. For example, the cassette 200 may omit dialysate fluid circuit and its components if the cassette is intended for CVVH and/or SCUF modes and the disposable set may therefore omit the dialysate fluid. In some embodiments, the fluid circuits may include different sizes, different paths, arrangement and/or configuration of the components along tire respective paths. For example, the fluid circuits may include additional pumps, sensors, filters, among others; may include alternative pumps, sensors, filters, among others; may omit pumps, sensors, filters, among others; or any combination thereof. By way of another examples, the cassette(s) configured for pediatric patients may include components (such as the conduits and pump chambers; that are smaller than the cassette(s) configured for adult patients and can thereby more effectively and efficiently process smaller volumes.

Figure 6:
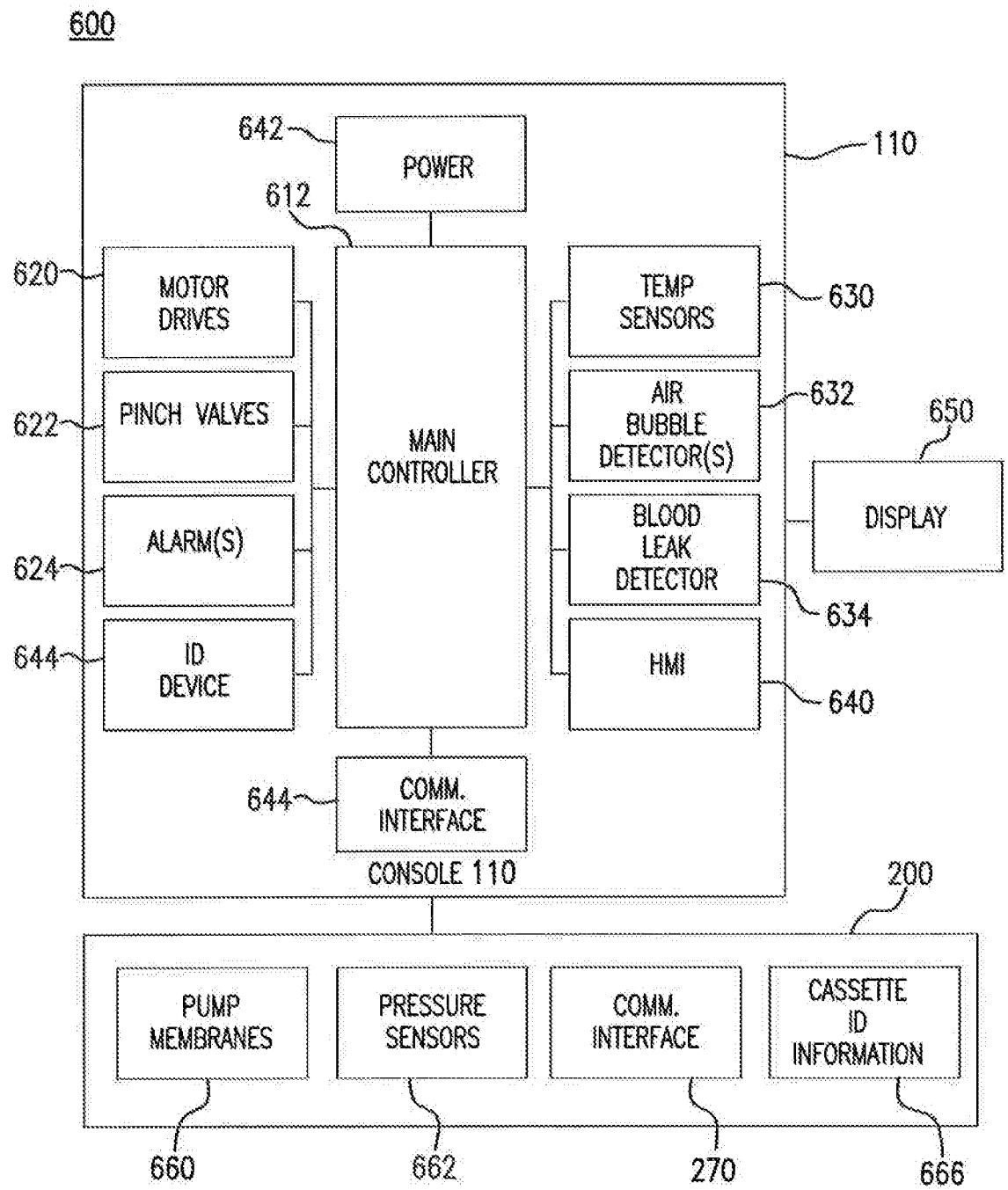
FIG. 6 shows an overview of the system components according to embodiments.

Although not shown, the cassette 200 may also include one or more vents disposed within the housing configured to vent any particles that may be introduced into the system. The cassette 200 may also include additional and/or alternative components In some embodiments, the console 110 may include components that are configured to control the fluid through the plurality of fluid paths included in the cassette 200, monitor the sensors of the cassette 200 via the electrical communication interface 270, monitor parameters of the fluid flow through the fluid circuits, among others, or a combination thereof when the cassette 200 is mated with the console 110. FIG. 6 shows an exemplary overview 600 of the components of the console 110 that electrically and/or mechanically interface with the components of the cassette 200 to control the medical fluid treatment therapy by controlling and monitoring operation of the fluid through the flow paths included in a cassette according to some embodiments. In some embodiments, the console 110 and/or cassette 200 may include different components that are capable of interfacing to control the medical fluid treatment therapy. For example, the console 110 and/or the cassette 200 may omit one or more components, include additional and/or alternative components, among others, or a combination thereof.

As shown in FIG. 6, the console MO may include a main controller 612 configured to control and/or monitor the components of the console 110, including the operations/interactions of some of the components of the console 110, with respect to the cassette 200 and the fluids moving through the cassette 200 to control the delivery of the medical fluid treatment therapy. The main controller 612 may be a computing device. By way of example, the main controller 612 may be a processor (e.g., central processing unit, a processor, microprocessor, etc.) that is coupled directly or indirectly to memory (not shown). The memory may include but is not limited to random access memory (RAM), read only memory (ROM), disk drive, tape drive, etc., or a combination thereof. The memory may be configured to store programs and data, for example, related to the different medical fluid treatment therapies.

Although not shown, the console 110 may include an input/output interface configured to receive information for one or more input devices (e.g., a keyboard, a mouse, and the like) and convey information to a display and other output devices.

In some embodiments, the console 110 may include a power supply 642, such as an electrical power supply. The console 110 may include and/or be connected to a display 650. By way of example, the display 650 may be integrated with the console. In another example, the console 110 may be wired and/or wirelessly connected to a separate display 650. In some embodiments, the display 650 may be touchscreen display. In some embodiments, the console 110 may include audible and/or visual alarms 624 based on the operation.

In some embodiments, the console 110 may include a plurality of actuators 620 and a plurality of pairs of pinch valves 622 to control the flow of the fluid through the respective circuit. Each pump and pair of pinch valves may be configured to interface with a pump chamber and respective pair of valve receiving members, respectively. In some embodiments, the number of actuators and sets of pinch valves may correspond to the number of available fluid circuits to be included in the cassette. By way of example, the console 110 may include four pumps and four pairs of pinch valves. The console 110 may dispose an actuator and pair of pinch valves on the panel 111 to interface with each pump membrane and corresponding valve receiving members disposed within each fluid circuit. In some embodiments, the console 110 may include more or less pumps and/or pinch valves.

In some embodiments, each actuator 620 may be configured to interface with the respective pump membrane. In some embodiments, each actuator 620 may have a shape complimentary to the pump membrane. In some embodiments, the actuator 620 may include a driving piston controlled by a motor. The actuator 620 may be a linear actuator. In some embodiments, the motor(s) controlling the actuator may include an accurate position determining mechanism configured to provide precision pumping action to achieve very low flow and precise pumping rates. In some embodiments, the pump may include different components. In some embodiments, the gearing ratios and speed for each motor may be configured to achieve the above given flow rates and range of operation.

By way of example, the actuator 620 may be disposed in the console 110 so to be substantially flush with the panel 111 when in resting position and configured to protrude from the panel 111 when in driving position. In the resting position, the actuator 620 may be configured to have substantially no contact with the respective pump membrane. In some embodiments, the actuator for the replacement fluid circuit and tire actuator for the ultrafiltrate circuit may be coupled to deliver substantially equal quantities of the replacement fluid and ultrafiltrate fluid, respectively.

Figure 4:
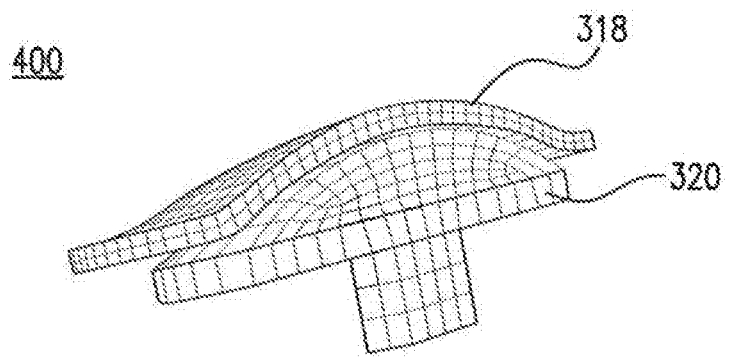
FIG. 4 shows another view of the pump interface shown in FIG. 3 according to some embodiments.

FIGS. 3 and 4 show examples 300 and 400 of the pump 320 with respect to a pump membrane 318 according to some embodiments. FIG. 1 shows the pump 320 in the driving position. As shown in FIG. 4, the pump 320 may be configured to directly contact and push against tire pump membrane 318 when in the driving position. The pump can be configured to cause the fluid to be pumped out of the pump chamber when in the driving position and to cause the fluid to fill the pump chamber when in the resting position.

Figure 5:
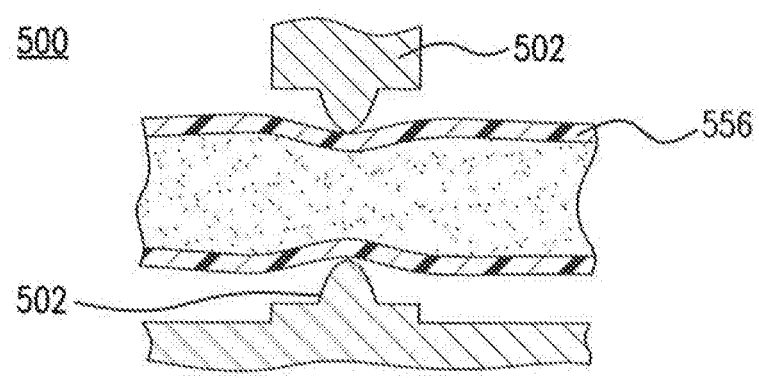
FIG. 5 shows an example of a pinch valve interface with the cassette according to embodiments.

In some embodiments, the flow direction in the circuit can be controlled through use of pinch valves on the inlet and outlet ports of each pump membrane to maintain the flow direction to be unidirectional. In some embodiments, the pinch valves may be precisely controlled based on the direction required and position of the actuator (e.g., motor rotor). In some embodiments, the pinch valves may be made of a sterile, biocompatible material, such as polished acrylic. FIG. 5 shows an example 500 of a pinch valve 502 with respect to the corresponding pinch valve receiving member 556 (e.g., an area of exposed tubing adjacent to a pump membrane). FIG. 5 shows the pinch valve 562 in a closed position.

In some embodiments, the controller 612 may be configured to control the movement of each actuator 620 (e.g., via a motor drive/motors) and pair of pinch valves 622 to cause fluid to flow through the respective circuit. In some embodiments, the flow direction can be controlled through the use of pinch valves disposed at the inlet and outlet ports of each pump to maintain the flow direction to be unidirectional.

By way of example, the controller 612 may synchronously control each actuator pump and pair of pinch valves 622 to cause the filling and expulsion of the fluid into and out of the respective pump chamber. For example, when the valve prior to the pump chamber is open and the valve alter the pump membrane is closed (e.g., as shown in FIG. 5), the controller 612 may cause the actuator 620 to downstroke to the resting position to remove any mechanical pressure from the pump chamber thereby causing the pump chamber to return to its initial position (e.g., as shown in FIG. 4). Once the actuator is in the resting position, the pump chamber can fill with a fluid for a period of time. After which, the controller 612 may cause the valve prior to the pump chamber to close and the valve after the pump to open and the actuator to upstroke to the driving position (e.g., shown in FIG. 4) to cause the fluid to be expelled from the chamber.

In some embodiments, the console 110 may include a plurality of fluid sensors and/or detectors configured to directly and/or indirectly engage one or more portions of the paths (e.g., tubing) of the cassette 200 to detect or measure the fluid characteristics of the fluid(s) along dial respective flow path. The fluid characteristics include but are not limited to temperature (e.g., sensors 630), air bubbles (e.g., sensor 632), leaks (e.g., sensor 634), or a combination thereof. In some embodiments, live console may include additional sensors, include alternative sensors, omit any of the sensors, among others, or any combination thereof. The sensors may be configured to interlace with the cassette when the cassette is properly mated with the console. In some embodiments, the sensors may be configured to directly or indirectly sense the fluid conduits of the cassette. For example, the sensors may be disposed on the console so as to surround and contact a portion of the tubing along a specific portion of a circuit. By way of another example, the sensors may be disposed so as to be in proximity to a portion of the tubing along a specific portion of the circuit.

In some embodiments, the controller 612 may cause one of the pinch valves to move to a closed position to stop the flow of fluid in a circuit if the respective sensor detects hubbies and/or leaks. In some embodiments, the console 110 may also include an additional pinch valve to be paired with each sensor to stop the flow of fluid when bubbles and/or leaks are detected in the respective circuit.

In some embodiments, the controller 612 may also alert the operator by causing the appropriate visual and/or audible alarms 624 to be activated when the controller detects a malfunction and/or improper operation of the cassette 200, the fluid delivery, and/or the console 110 is detected.

In some embodiments, the console 110 may include one or more air bubble detectors 632 to interface with one or more the fluid circuits to detect any air bubbles in the fluids flowing through the paths. In some embodiments, one or more bubble detectors 632 to detect the presence of air bubbles in the blood entering the cassette 200 (e.g., from the patient via the line 102) and in the filtered blood and/or replacement fluid exiting the cassette 200 (e.g., to the patient via line 104). In some embodiments, the detectors may be capable of any non-invasive detector capable of detecting the presence of micro-air bubbles sized (0.3 ul to 0.5 ul). In some embodiments, the sensor parameters may depend on the size of the cassette due to the difference in tube size.

In some embodiments, the air bubble detector(s) may be configured to directly engage the cassette 200. By way of example, each air bubble detector may be disposed and protrude from the panel 111 to at least partially surround and/or clamp a specific portion of the tubing along a path of the cassette 200. By way of example, the housing 202 may include an interface section (e.g., cut-out, opening, etc.) that corresponds to each specific portion for engagement by the respective air bubble detector.

As shown in FIG. 1, the console 110 may include a first bubble detector 112 disposed to interface with the blood flow circuit 210 of the cassette 200, a second bubble detector 118 disposed to interface with the return circuit 240 of the cassette, among others, or any combination thereof. In some embodiments, the first air bubble detector 112 may be disposed on lire panel 111 to interface with a portion of the path (tubing) 218 between the inlet port 211 and the pressure sensor 212 of the cassette 200. In some embodiments, the second air bubble sensor 118 may be disposed on the panel 111 to interface with a portion of the path (tubing) 268 between the pressure sensor 262 and the outlet port 269. The first and second bubble detectors may be configured to detect the presence of air bubbles in the blood.

In some embodiments, tire console 110 may include a third bubble detector 116 to detect the presence of air bubbles in the dialysate fluid entering the cassette 200 (e.g., from the container 144). In some embodiments, the third air bubble detector 116 may be disposed on the panel 111 to interface with a portion the path (tubing) 218 between the input port 239 and the bubble trap 232 of the cassette 200.

In some embodiments, as shown in FIG. 1, the console 110 may include a blood leak detector 124 disposed to interface with the ultrafiltrate circuit 220 of the cassette 200 to detect any blood cells exiting with lire ultrafiltrate from live fiber 130. In some embodiments, the blood leak detector 124 may be disposed on the panel 111 to interface with a portion of Ute path (tubing) 228 between the inlet port 221 and the pressure sensor 222 of the cassette 200. In some embodiments, the blood leak detector 124 may be disposed and protrude from the panel 111 to at least partially surround and/or clamp a specific portion of the tubing at an interface section along a path of the cassette 200. The blood leak detector 124 can be any blood leak detector. By way of example, the blood leak detector may be a non-invasive optical sensor to detect the presence of red blood cells in the ultrafiltrate circuit 200.

In some embodiments, the console lit) may include a temperature sensor 126 disposed to interface with the return circuit 240 to ensure that the dialysate is maintained at the substantially the same temperature as the returned circuit (e.g., returned blood). In some embodiments, the sensor 126 may be disposed on the panel 111 to interface with a portion of the path (tubing) 258 between the bubble detector/filter/trap 252 and the pump chamber 254 of the cassette 200. In some embodiments, the temperature sensor 126 may be in proximity of a portion of the tubing of the circuit 230.

In some embodiments, the console 110 may also include one or more heaters. In some embodiments, the heater may be disposed on the dialysate fluid circuit before the temperature sensor.

In some embodiments, the console 110 may include a plurality of communication interfaces 644. The communication interface 644 may include and is not limited to an Ethernet interface, usb interface, serial interface, wireless interface (e.g., wi-fi), among others, or any combination thereof. The communication interfaces 644 may include an electrical communication interface that is complimentary to the electrical communication interface 270 of the cassette 200. By way of example, one electrical communication interface may be a spring loaded connector (e.g., pogo pin), USB, among others, and the Other electrical communication interlace may be the complimentary port. In operation, through the electrical communication interfaces, the console 110 may receive the pressure measurements form the pressure sensors 662 (e.g., pressure sensors 212, 222, and 262) disposed on the cassette 200. In this way, the main controller 612 may monitor the pressure and cause the alarms to sound when a pressure error is detected.

In some embodiments, the system 109 may include an identification device to aid in authentication, identification, and tracking of the medical therapy treatment procedure. In some embodiments, the cassette 200 may include identification information 666 and the console 110 may include a complimentary reading device 644 (e.g., a RFID reading device). In some embodiments, the identification information may include but is not limited to identification number of the cassette, size of cassette (e.g., patient or pediatric), type of cassette (e.g., CVVH, CVVHD, CVVHDF, SCUF modes), among others, or any combination thereof.

In some embodiments, the console 110 may automatically configure the treatment parameters based on the identification information (e.g., the size and type of cassette). For example, the console 110 may automatically configure the upper and lower limits, for example, for flows and pressures, for the fluid Circuits included in that type of cassette based on the indicated size. By including the identification information, the system can allow for a safer and faster setup of the CRRT procedure.

In some embodiments, the console 110 may include a human machine interface (HMI) 640. In some embodiments, the instructions for the may be programmed and stored in the memory of the console 110. The HMI may be programmed to control or provide instructions to control the system 100 based on inputs entered by the user and/or provided by the cassette 200. FIGS. 8-12 show examples of interfaces.

Figure 7:
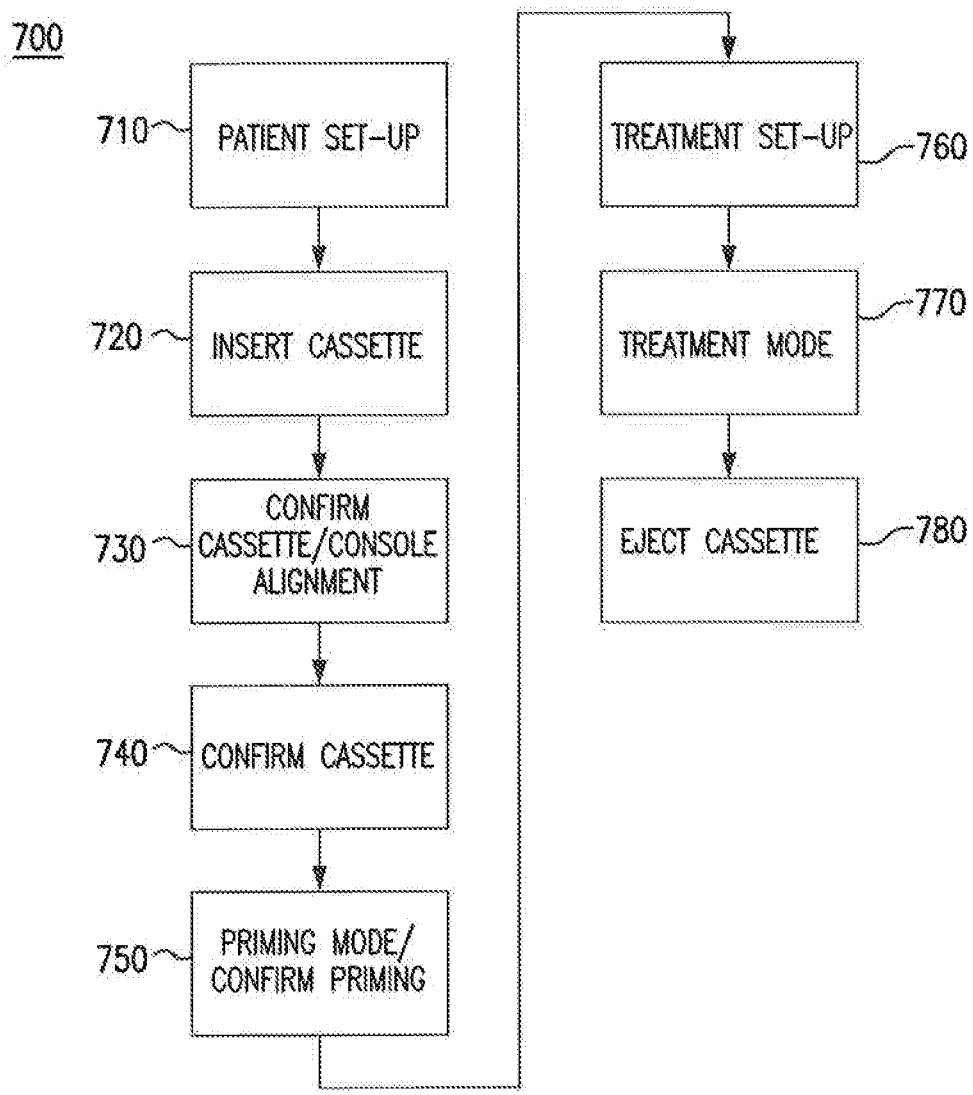
FIG. 7 shows a method of operating the system according to embodiments.

FIG. 7 shows a method 700 of operation of the system 100 with respect to a treatment of a patient. After the console 110 is powered on, tire method 700 may include a step of patient set-up 710. In some embodiments, the console 110 via a touch-screen display may prompt the user to obtain the supplies necessary for tire treatment. In some embodiments, the console 110 may request a plurality of patient information to determine the appropriate cassette. FIG. 8 shows an example 800 of a new patient-set up screen. Based on tire patient information inputted (e.g. weight of patient and desired treatment mode), the console 110 will determine the type of cassette (e.g., size (e.g., pediatric or adult) and treatment mode) to be inserted, for example, by identifying the type and other indicia (e.g., color).

Next, the method 700 may include a step 720 of inserting a cassette onto tire console 110. The system may then include a step of confirming the cassette. In some embodiments, the method 700 may include a step 730 confirming proper cassette/console alignment. For example, the sensors of the console may check to see if they receive the default electrical signal. In this example, if the cassette is not properly aligned, then the conduits of the cassette may not properly mate with the sensor so the sensors may not receive the default electrical signals. If the controller 612 of the console 110 determines that any of the sensors did not send the default electrical signal, then console 110 can issue an error message regarding the cassette misalignment and request that the cassette to be adjusted/re-inserted.

After the controller 612 of the console lift confirms that the cassette 200 is properly aligned with the panel 111, the console 110 may then confirm whether tire correct cassette has been inserted (step 740). In some embodiments, the identification device of the console 110 may read the identification information provided on the cassette. For example, an RFID receiver provided on the console 110 may read the RFID chip provided on the cassette to determine the type of cassette inserted. The console 110 then can compare the cassette-type indicated by the identification information on the cassette to the console-suggested cassette type based on the patient information (step 710). For example, the console 110 determines that the inserted cassette docs not correspond to the console suggested cassette, the console 110 may prompt the user to: change the treatment selections by either overriding the size different (e.g., override the weight) and/or changing the therapy mode; and/or to insert another cassette.

In some embodiments, the sensors disposed on the cassette can be configured to generate a signal to determine whether the correct cassette is mated with the console. For example, if the user indicates the CVVHD mode in the patient set-up but inserts a cassette configured for the CVVH mode, at least one sensor can receive a signal indicating that the corresponding conduit (tubing) is missing and the console 110 can prompt the user accordingly.

After the console 110 confirms that the correct cassette is inserted and/or receives an override from the user, the method 700 may include the initiation of the prime mode and/or confirmation that the cassette has been primed (step 750). The prime mode can prepare the system for the medical fluid delivery by confirming that there are no bubbles in any of the fluid circuits of the cassette.

To initiate the priming mode, the system can prompt the user to attach a specific size of priming fluid and initiate by pushing start on the display. In some embodiments, the system 100 operates similarly during the priming mode as the treatment mode. After the priming mode is initiated, the console 111 will cause the priming fluid to flow through all the fluid-circuit lines included in the cassette (e.g., dialysate, replacement fluid and blood) by causing the actuators and valves to engage the pump membrane and valve receiving members disposed in those lines at a rate that can be faster than the treatment mode. The controller can process the signals generated by the respective bubble detectors to monitor the progress of the priming mode and provide an estimated time to complete the priming mode. After the controller of the console receives a "no bubble" signal from the bubble detectors, the console will indicate that the priming mode has been completed.

In some embodiments, the console 110 may configured to confirm that the cassette has been primed. The RFID chip on the cassette may indicate that the priming mode was performed. For example, the RFID receiver provided on the console 110 may read the RFID chip provided on the cassette to determine whether the priming mode has been performed and/or whether a priming mode needs to be performed (step 750). The cassette may include additional valves that are configured to prevent the draining (leaking) of the priming-fluid from the cassette while it is transferred/stored.

In some embodiments, the priming mode for a cassette may be performed on another console before being loaded into the console 110 for treatment (step 720). This way, a cassette may be ready for treatment for a patient and can avoid the delay associated with the priming step, before the beginning of CVVH (or CVVHD or CVVHDF) on the patient. In some embodiments, the other console may be configured for only the priming mode. Temperature controls may be enabled to make sure that the priming fluid inside the cassette is maintained within correct temperature range before being used on the patient.

In some embodiments, the cassette may be packaged with the priming fluid inside the tubes in the cassette. For example, the cassette may be primed at the manufacturing facility. The packaged cassette may be loaded into the console 110 for treatment (step 720).

Next, the user may be prompted to input one or more treatment parameters (step 760). The one or more treatment parameters may include but are not limited to flow rates (e.g., blood circuit, ultrafiltrate circuit, and/or dialysate circuit), pressure thresholds (e.g., for the blood circuit, return circuit and/or ultrafiltrate circuit), among others, or any combination thereof. In some embodiment, the console 110 may store default parameters for any or all of the treatment parameters. FIGS. 9 and 10 show examples of user interfaces in which treatment parameters con be inputted.

In some embodiments, based on the inputted flowrates, the controller of the console 110 may determine the operation parameters for the actuator and corresponding pair of pinch of valves for each circuit line. Based on the inputted flow rates, the console 110 may determine the revolutions per minute (RPM). In some embodiments, the console 110 can operate the replacement fluid circuit using the same treatment and operation parameters for the ultrafiltrate circuit. In this way the console 110 can deliver substantially equal quantities of replacement fluid and ultrafiltrate.

After the treatment information is inputted, the console 110 may prompt the user to connect the patient to the cassette (via the arterial input and the venous output lines). Then, the treatment mode may be initiated (step 770). During the treatment mode, the console 110 can cause each actuator and corresponding pair of pinch valves to move according to the determined operation parameters to cause the fluids to flow through the respective fluid circuits at the desired flow rate. In some embodiments, the actuators and pair of pinch valves for the blood circuit may move according to the operation parameters for a short period of time before the actuators and pinch valves move other circuits start to move.

Also, during the treatment mode, the console 110 may monitor the fluid treatment for certain conditions. By way of example, the console 110 may monitor the console's sensors and the pressure signals from the pressure sensors of the cassette for the pressure, temperature, and flow rates. The console 110 may automatically operate according to specific operation protocols when the detected values are outside a sale limit. The operation protocols may be inputted by the user and/or default to the console 110. For example, if the console 110 determines that a sensor value is outside a safe limit, the console 110 may pause the machine and provide an error display. The error display may prompt the user to a specific location or potential error. By way of example, if the console 110 determines that one of the pressure sensors on the cassette reads a value beyond the safe limit, the console 110 may cause the machine to pause and stop any fluid motion to or from the patient, for example, by locking the pinch vales in place and stop the rotation of all motors.

During the end of the treatment mode, the user may be prompted regarding whether the blood disposed in the system should be returned to the patient or circulated before the cassette is disconnected. Tire user can also specify the volume of fluid to be returned to the patient.

After the treatment mode is completed, the cassette 200 may be removed (step 780). In some embodiments, the cassette 200 may be ejected from the console by inputting a button on the display.

Figure 12:
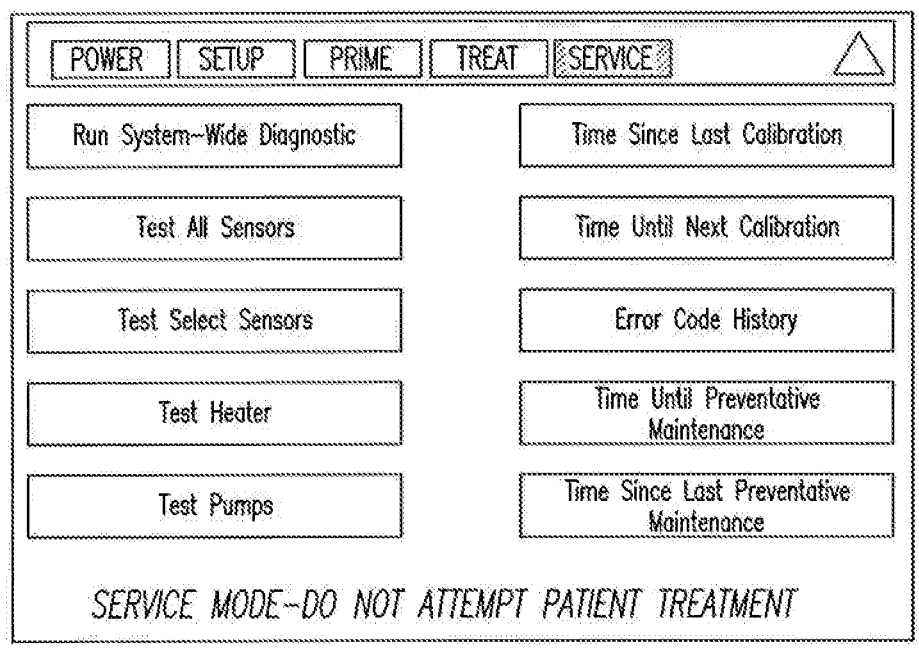

In some embodiments, the system 100 may include a service cassette to run diagnostics, for example, for troubleshooting, repairing, and/or calibration the components of the console 110. The service cassette may include the same components as the treatment cassette. When the service cassette is inserted, the console 110 may operate according to a service mode. During the service mode, the user can view the error history, preventive maintenance history, calibration history, calibration schedules for different sensors, among others, or any combination thereof. In some embodiments, the console 110 may cause signals to be sent to the pressure, temperature, bubble, blood-leak sensors, so that their responses can be recorded. FIG. 12 shows art example of a service mode interface.

While the disclosure has been described in detail with reference to exemplary embodiments, those skilled in the art will appreciate that various modifications and substitutions may be made thereto without departing from the spirit and scope of the disclosure as series forth in the appended claims. For example, elements and/or features of different exemplary embodiments may be combined with each other and/or substituted for each other within the scope of this disclosure and appended claims.

What is claimed is:

1. A medical fluid therapy delivery system, comprising:
a console configured to provide multiple medical fluid treatment types, the console having a panel, the console including a first combination of a first actuator and a first pair of pinch valves and a second combination of a second actuator and second pair of pinch valves, wherein the first actuator and the second actuator are disposed between a first pinch valve and a second pinch valve of the first pair of pinch valves and the second pair of pinch valves respectively, the first and second actuators configured to move with respect to the panel; and
a first disposable cassette configured to mate with the first combination and a second disposable cassette configured to mate with the second combination, the first disposable cassette structured for a first medical fluid treatment type and the second disposable cassette structure for a second medical treatment type different from the first medical fluid treatment type, wherein each disposable cassette includes a plurality of fluid circuits, each fluid circuit includes a path being defined by one and more inlets and outlets in which a fluid flows, and a pump chamber disposed between a first valve receiving member and a second valve receiving member along the path;
wherein the panel is configured to mate separately with both of the first and the second disposable cassettes so that:
the first actuator of the first combination aligns with a first pump chamber of the first disposable cassette and the first pair of pinch valves align and interface with the corresponding first valve receiving member and the second valve receiving member of the first disposable cassette; and
the second actuator of the first combination aligns with a second pump chamber of the second disposable cassette and the second pair of pinch valves align and interface with the corresponding first valve receiving member and the second valve receiving member of the second disposable cassettes,
wherein the console is configured to control the movement of the actuators and the first and the second pinch valves of each combination to control a flow of the fluid in the path when the disposable cassettes and the panel are mated.

2. The system according to claim 1, wherein:
each of the disposable cassettes includes one or more pressure sensors disposed along the path of one or more fluid circuits and an electrical communication interface that communicates with each pressure sensor;
the console includes one or more fluid sensors to measure fluid characteristics of the flow along the path of one or more fluid circuits and an electrical communication interface that is complimentary to the electrical communication interface of the disposable cassette; and
when either the first or the second disposable cassette and the panel are mated, the electrical communication interface of the first or the second disposable cassette is configured to transmit the pressure to the console via the electrical communication interface of the console.

3. The system according to claim 1, further comprising:
a filter; and
one or more containers;
wherein when either the first or the second the disposable cassette and the panel are mated, the first or the second disposable cassette is configured to be disposed on the panel between the filter and the one or more containers so that the filter and the one or more containers are disposed adjacent to a first side and a second side of the first or the second disposable cassette, respectively.

4. The system according to claim 3, further comprising:
a dialysate circuit configured to connect to the filter.

5. The system according to claim 3, wherein:
each fluid circuit is configured for unidirectional fluid flow along the path; and
the fluid circuits include a blood circuit, an ultrafiltrate circuit, a replacement fluid circuit and a return circuit.

6. The system according to claim 5, wherein the blood circuit includes an inlet and an outlet disposed on the first side.

7. The system according to claim 5, wherein a length of the path of the blood circuit is shorter than a length of the paths of the ultrafiltrate circuit, the replacement fluid circuit and the return circuit.

8. The system according to claim 5, wherein the fluid circuits are disposed with respect to the top of the first or the second disposable cassette when mated with the console as follows: the blood circuit, the ultrafiltrate circuit, the replacement fluid circuit and the return circuit.

9. The system of according to claim 1, wherein the first disposable cassette is structured for use with an adult and the second disposable cassette is structured for use with a child.

10. A medical fluid therapy delivery system configured to apply multiple types of fluid renal treatment, comprising:
a console comprising:
a panel including a plurality of combinations of an actuator and a pair of pinch valves, the actuators configured to move with respect to the panel; and
an identification reading device; and
a plurality of disposable cassettes configured to mate with the panel of the console, wherein each of the plurality of disposable cassettes are configured for different fluid renal treatment types, wherein each of the plurality of the disposable cassettes comprises:
a plurality of fluid circuits, each fluid circuit includes a path being defined by one and more inlets and outlets in which a fluid flows;
a pump chamber disposed between a first valve receiving member and a second valve receiving member along the path; and
an identification device used to identify the type of fluid renal treatment for which the disposable cassette is configured for use,
wherein the panel is configured to mate separately with the plurality of disposable cassettes, and wherein the identification reading device is configured to read the identification device of each disposable cassette to determine the fluid renal treatment for the console to perform.

11. The medical fluid therapy delivery system of claim 10, wherein the plurality of fluid circuits of each disposable cassette corresponds to the type of fluid renal treatment.

12. The medical fluid therapy delivery system of claim 10, wherein the identification device is an RFD.

13. The medical fluid therapy delivery system of claim 10, wherein the console further comprises a main controller in communication with the identification reading device, wherein upon receiving the identification of the type of the type of fluid renal treatment associated with the disposable cassette, the main controller is configured to automatically set up the treatment parameters for the fluid renal treatment.

14. The medical fluid therapy delivery system of claim 10, wherein each disposable cassette further comprises a pump chamber, wherein at least one of the plurality of combination of actuators and pinch valve pairs is configured to align with the pump chamber of the disposable cassette, wherein based upon the identification of the disposable cassette mated with the panel, the console is further configured to control the movement of the actuator and the first and the second pinch valves to control a flow of the fluid in the path when the disposable cassette and the panel are mated.

15. The medical fluid therapy delivery system of claim 10, wherein the multiple fluid renal treatment therapy comprises continuous renal replacement therapies (CRRTs).

16. The medical fluid therapy delivery system of claim 15, wherein the CRRTs comprise slow continuous ultrafiltration (SCUF) therapy, continuous veno-venous hemofiltration (CVVH) therapy, continuous veno-venous hemodiafiltration (CVVHDF) therapy, and continuous veno-venous hemodialysis (CVVHD) therapy.

17. A medical fluid therapy delivery system configured to apply multiple fluid renal treatment types, comprising:
a plurality of disposable cassettes configured to mate with the panel of the console, wherein each of the plurality of disposable cassettes are configured for use with different fluid renal treatment types, wherein each of the plurality of the disposable cassettes comprises:
a plurality of fluid circuits, each fluid circuit includes a path being defined by one and more inlets and outlets in which a fluid flows;
a pump chamber disposed between a first valve receiving member and a second valve receiving member along the path; and
an electrical communication interface that communicates with each pressure sensor; and
a console comprising:
a panel configured to mate with the plurality of disposable cassettes;
one or more fluid sensors to measure fluid characteristics of the flow along the path of one or more fluid circuits; and
a plurality of electrical communication interfaces complimentary to the electrical communication interface of each disposable cassette, wherein the console is configured to receive signals from the fluid sensors through the electrical communication interfaces to identify the disposable cassette and type of fluid renal treatment associated with the disposable cassette.

18. The medical fluid therapy delivery system of claim 17, wherein the console further comprises a human machine interface configured to receive instructions for operation of the fluid renal treatment, wherein the console is configured to confirm the instructions provided match the disposable cassette.

* * * * *